United States Patent [19]

Meyer

[11] 4,041,226
[45] Aug. 9, 1977

[54] CHROMIUM TRIS-DIORGANO-ORTHOPHOSPHATE-ALKYL ALUMINUM HALIDE CATALYSTS FOR OLEFIN POLYMERIZATION AND ALKYLATION OF AROMATIC COMPOUNDS

[75] Inventor: Jeffrey G. Meyer, Adrian, Mich.

[73] Assignee: Anderson Development Company, Adrian, Mich.

[21] Appl. No.: 634,592

[22] Filed: Nov. 24, 1975

Related U.S. Application Data

[60] Division of Ser. No. 532,010, Dec. 12, 1974, Pat. No. 3,969,272, which is a continuation-in-part of Ser. No. 319,621, Dec. 29, 1972, Pat. No. 3,907,849.

[51] Int. Cl.$^2$ .............. C08F 2/06; C08F 4/62; C08F 10/00

[52] U.S. Cl. .................. 526/144; 252/431 P; 526/161

[58] Field of Search ............. 526/144, 161; 252/431 P

[56] References Cited

U.S. PATENT DOCUMENTS

| 3,474,080 | 10/1969 | Rekers | 526/161 |
| 3,595,843 | 7/1971 | Huerta et al. | 526/161 |
| 3,725,444 | 4/1973 | Huerta et al. | 526/161 |
| 3,910,976 | 10/1975 | Fein | 252/431 P |
| 3,969,272 | 7/1976 | Meyer | 252/431 P |

Primary Examiner—Alan Holler
Attorney, Agent, or Firm—Richard M. Howell

[57] ABSTRACT

The reaction product of a chromium tris-diorganoorthophosphate and an alkyl aluminum halide is a catalyst for olefin polymerization and for alkylation of aromatic hydrocarbons with olefins.

9 Claims, No Drawings

CHROMIUM TRIS-DIORGANO-ORTHOPHOSPHATE-ALKYL ALUMINUM HALIDE CATALYSTS FOR OLEFIN POLYMERIZATION AND ALKYLATION OF AROMATIC COMPOUNDS

CROSS-REFERENCE TO RELATED APPLICATION

This application is a division of my earlier U.S. application Ser. No. 532,010, filed Dec. 12, 1974, now U.S. Pat. No. 3,969,272, which was a continuation-in-part of my earlier U.S. application Ser. No. 319,621, filed Dec. 29, 1972, now U.S. Pat. No. 3,907,849.

BACKGROUND OF THE INVENTION

Alkyl aromatics are known to be prepared by the reaction of aromatic hydrocarbons with olefins in the presence of catalyst mixtures of alkyl aluminum halides and heavy metal halides as set forth in U.S. Pat. Nos. 3,129,255; 3,129,256 and 3,134,822. High molecular weight polymers and copolymers of olefins are known to be prepared in the presence of vanadium oxy diethyl phosphate as set forth in U.S. Pat. Nos. 3,595,843 and 3,595,844.

It is a principal object of this invention to provide a new catalyst combination for such alkylation and polymerization. A further object of this invention is to provide a method for activating this catalyst composition.

SUMMARY OF THE INVENTION

This invention comprises a combination catalyst for olefin polymerization and for alkylation of aromatic hydrocarbons with olefins, said catalyst consisting essentially of the reaction product of (A) a chromium tris-diorgano-orthophosphate of the general formula Cr[OP(O)(OR)$_2$]$_3$ in which each R is a nonaromatic hydrocarbon group free of aliphatic unsaturation, i.e. an alkyl or cycloalkyl group, containing one to eight, preferably two to four, carbon atoms or a non-aromatic hydrocarbon ether group free of aliphatic unsaturation, i.e., an alkoxyalkyl group, containing three to six carbon atoms or a chlorinated or brominated derivative of any of such groups and (B) an alkyl aluminum halide of the general formula R'$_c$Al X$_d$ in which each R' is an alkyl group of one to six carbon atoms, each X is a halogen atom, preferably chlorine or bromine, each of $c$ and $d$ is 1 or 2 and the total of $c$ and $d$ is 3. The mol ratio of (A) to (B) can range from 1:1 to 1:20 but is preferably in the range of 1:8 to 1:12 unlike the ratios set forth in the above-noted U.S. patents relating to alkylation.

This invention further comprises the use of the abovedescribed catalyst combination in a method for polymerization and/or alkylation consisting essentially of (1) mixing the catalyst combination of (A) and (B) described with (C) a mono- or di-olefin which can be any aliphatic, cycloaliphatic or aromatic hydrocarbon preferably containing no more than about 20 carbon atoms, more preferably no more than about 12 carbon atoms, either alone or with (D) an aromatic hydrocarbon containing from 6 to 14 aromatic carbon atoms and, optionally, substituted with up to about four lower alkyl groups or other non-interfering substituents such as, for example, oxygen-free anions of non-metallic inorganic acids such as chlorine atoms, bromine atoms and nitrile groups at a temperature and pressure and for a time sufficient to cause reaction of (C), alone or with (D), and (2) separating the resulting product. The total amount of (A) and (B) is present in an amount of from about 0.0001 to 0.01 total mol per mol of combined (C) and (D). The ratio of (C) to (D) depends on whether the primary end-product is an alkylated aromatic compound or a polymerized olefin. This system operates spontaneously as soon as the components are mixed. Generally, the system temperature can range from 0° to 250° C., preferably 50° to 150° C., and the system pressure can range from 1 to 500 psig., preferably 10 to 100 psig. The desired reaction can take fron one minute to 24 hours, but the reaction generally takes from 5 minutes to 2 hours.

DESCRIPTION OF THE PREFERRED EMBODIMENTS

The chromium tris-diorgano-orthophosphates employed herein have the general unit formula Cr[OP(O)(OR)$_2$]$_3$, either monomers or polymers thereof, principally coordination polymers, composed preferably of from one to ten units. These compounds and their preparation are more fully described and claimed in the aforementioned United States application Serial No. 319,261.

In these chromium compounds each R can be, for example, any alkyl, alkoxyalkyl or cycloalkyl group of up to about eight carbon atoms. Special examples of such groups include methyl, ethyl, propyl, isopropyl, butyl, isobutyl, tert-butyl, pentyl, isopentyl, hexyl, isohexyl, 2,2,4-trimethylpentyl, 2-methylpentyl, 2,2-dimethylbutyl, 2,3-dimethylbutyl, heptyl, 2-methylhexyl, 3-methylhexyl, 3,3-dimethylpentyl, octyl, 2,3-dimethylhexyl, 2,4-dimethylhexyl, 2-ethylhexyl, 2-ethylbutyl, methoxyethyl, ethoxyethyl, butoxyethyl, cyclohexyl, cyclobutyl and cyclopentyl groups and chlorinated and brominated derivatives such as the 3-chloropropyl, chlorocyclohexyl and 2,3-dibromopropyl groups.

Examples of suitable chromium compounds include:

Chromium tris (dipropyl orthophosphate), chromium tris (di-n-octyl orthophosphate), chromium tris (di-4,4-dimethylhexyl orthophosphate), chromium tris (di-2-ethylhexyl orthophosphate), chromium tris (diethyl orthophosphate), chromium tris (diisobutyl orthophosphate), chromium tris (monobutyl mono-tert-butyl orthophosphate), chromium tris (monopentyl mono-2-methylpentyl orthophosphate), chromium tris (di-3-methylhexyl orthophosphate), chromium tris (mono-2-ethylhexyl mono-3-methylhexyl orthophosphate), chromium tris (di-2,3-dimethylhexyl orthophosphate), chromium tris (dicyclohexyl orthophosphate), chromium tris (dibutyl orthophosphate), chromium bis (diethyl orthophosphate) mono (diisohexyl orthophosphate), chromium tris (di-3,3-dimethylpentyl orthophosphate), chromium bis (monoheptyl monohexyl orthophosphate) mono (monoheptyl monooctyl orthophosphate), chromium tris di-2,2,4-trimethylpentyl orthophosphate), chromium tris (di-2-ethoxyethyl orthophosphate), chromium tris (dicyclopentyl orthophosphate), chromium tris (di-2,2-dimethylbutyl orthophosphate), chromium bis (monopropyl monobutyl orthophosphate) mono (monoamyl monohexyl orthophosphate), chromium tris (dicyclohexyl orthophosphate), chromium tris (dicyclobutyl orthophosphate), chromium tris (d-3-chloropropyl orthophosphate), chromium tris (bis-2,3-dibromopropyl orthophosphate and chromium tris (di-2-chloroethyl orthophosphate).

The chromium tris-diorgano-orthophosphates of this invention are particularly useful in combination with alkyl aluminum halides as a catalyst system for olefin polymerization and alkylation of aromatic hydrocarbons. More specifically, this catalyst system consists essentially of the reaction product of (A) one or more chromium tris-diorgano-orthophosphates of the formula Cr [OP (O) (OR)$_2$]$_3$ as described above and (B) one or more alkyl aluminum halides of the general formula R'$_c$Al X$_d$ in which each R' is an alkyl group of one to about six carbon atoms, each X is a halogen atom, preferably chlorine of bromine, each of $c$ and $d$ is 1 or 2 and the total of $c$ and $d$ is 3, the mol ratio of (A) to (B) being in the range of 1:1 to 1:20, preferably 1:8 to 1:12.

The alkyl aluminum halides are primarily the compounds R' Al X$_2$, R'$_2$Al X and mixtures thereof including the mixtures of the formula R'$_3$Al$_2$X$_3$ usually referred to as the sesquihalides. Each R' can be, for example, a methyl, ethyl, propyl, iso-propyl, n-butyl, sec-butyl, tert-butyl, pentyl or hexyl group. Each X can be fluorine, chlorine, bromine or iodine. Examples of suitable alkyl aluminum halides include diethylaluminum chloride, n-butylaluminum dibromide, ethyl aluminum sesquichloride, methyl aluminum sesquichloride, ethyl aluminum sesquibromide, ethyl aluminum sesquifluoride and the like.

The catalyst composition of (A) and (B) is simply prepared by mixing the components. The components can be mixed prior to addition to the alkylation or polymerization reaction system or can be added simultaneously or separately to such reaction system. While there may be the desired reaction in five minutes or less, it is known that the desired reaction takes place in no more than two hours.

The combination catalyst system is used in the method comprising (1) mixing the reaction product of (A) and (B) described above with (C) one or more mono- or di-olefins which can be any aliphatic, cycloaliphatic or aromatic hydrocarbons preferably containing no more than about 20 carbon atoms, more preferably no more than about 12 carbon atoms, alone or with (D) an aromatic hydrocarbon containing from 6 to about 14 aromatic carbon atoms, said hydrocarbon being optionally substituted with up to about four lower alkyl groups or other noninterfering substituents such as anions of non-metallic inorganic acids and nitrile groups, at a temperature and pressure and for a time sufficient to cause the reaction of (C) and (2) separating the resulting product.

Examples of suitable olefins (C) include ethylene, propylene, isobutylene, butene-1, cis-butene-2, trans-butene-2, pentene-1, hexene-1, cyclopentene, cyclohexene, cycloheptene, 4-methycyclooctene, 2-methylbutene-1, pentadecene-1, styrene, butadiene, isoprene, 3-vinylcyclohexene and the acyclic and cyclic terpenes. Substitution or inclusion of non-interfering groups as in acrylonitrile, methyl vinyl ether, vinyl chloride and chloroprene is not intended to put such olefins outside the scope of suitable olefins (C). The aromatic olefins are preferably limited to a maximum of 8 carbon atoms. The cycloaliphatic and aliphatic olefins are preferably limited to a maximum of about 6 carbon atoms.

Examples of suitable alkylatable aromatic hydrocarbons (D) include benzene, toluene, xylenes, chlorobenzene, dichlorobenzene, ethylbenzene, tetralin, cumene, diisopropylbenzenes, durene, naphthalene, isopropylnaphthalenes, 1,2,4-triisopropylbenzene, phenanthrene, biphenyl, bromobenzene, anisole, benzonitrile, benzofuran, 2-bromobiphenyl, 3,3'-dimethylbiphenyl and 1-chloronaphthalene.

The mol ratio of total (A) to (B) to total (C) and (D) can be as little as 0.0001:1 as taught in the prior art but preferably ranges from 0.001:1 to 0.01 to 1.

For simple polymerization of olefins (C) no aromatic component (D) need be present, especially for the polymerization of ethylene to a high polymer, but small amounts of component (D) may accelerate the polymerization reaction. In such cases the mol ratio of (D) to (C) should be less than 0.01:1, preferably no more than about 0.001:1.

For the alkylation of aromatic compounds (D) the mol ratio of (C) to (D) is generally about the same as the desired degree of substitution desired. If one mol of (C) is desired to react with one mol of (D), the ultimate mol ratio of (C) to (D) will be 1:1. If two mols of (C) are desired to react with one mole of (D), the ultimate mol ratio of (C) to (D) will be 2:1. With the thoroughly reacted catalyst combination of this invention the alkylation reaction of (C) and (D) takes place in preference to polymerization of the olefin (C) unless there is a large excess of (C) compounds compared to the available reactive sites on the compounds of (D).

The temperatures required for the alkylation and/or polymerization reactions with the catalyst combinations of this invention are not particularly critical with the catalyst combinations of this invention. Some heat may be necessary to initiate reaction such as heating to at least 30° C. The maximum temperature which can be employed is dependent on the melting points, boiling points and decomposition points of the catalytic components (A) and (B), the reacting components (C) and (D) and the products as well as the desired control over rate of reaction. For practical purposes, the maximum temperature is about 200° C. and the preferred temperature range is 40° C. to 100° C.

Ambient pressures are satisfactory generally ranging from atmospheric pressure to no more than about 50 atmospheres, preferably no more than 100 psig.

Under these conditions of temperature and pressure either the polymerization or alkylation reactions can be operated batchwise for from five minutes to four hours or more or these reactions can be run continually, especially where the products are in a different physical state than the reactants making possible continuous addition of reactants and continuous separation of product.

For these alkylation and/or polymerization reactions the reacting monomer or monomers may act as a solvent for the system. Alternatively, an inert solvent can be employed. While simple paraffin oils can be used, the halogeno-alkanes are preferred, particularly methylene chloride, chloroform, carbon tetrachloride and ethylene chloride.

The separation of the desired product is well within the skill of the art in that the desired product has a higher molecular weight than the reactants so that it can be precipitated out by cooling or other technique or can be selectively distilled.

Typically, for polymerization a reaction vessel is purged with some monomer (C) if gaseous or an inert gas such as nitrogen. Then enough of the alkyl aluminum halide (B) is added to dry the vessel. An inert solvent such as heptane may be added. The desired amount of components (A) and (B) are added, preferably in a mol ratio of 1:8 to 1:12, with monomer at ambient pressure at a sufficient rate to allow continuous reaction but not at such an excessive rate as to kill the reaction. Solid product is allowed to settle and is filtered off.

For alkylation the procedure is the same except that the desired aromatic compound (D) is added to the reaction vessel prior to adding (C).

The following examples are illustrative of the best presently-known methods of practicing this invention and are not intended to limit this invention the scope of which is delineated in the appended claims. Unless otherwise stated, all quantitative measurements are by weight.

EXAMPLE I

Preparation of Chromium (III) Tris (diethyl orthophosphate)

A mixture of 50.0 grams chrome alum $CrK(SO_4)_2 \cdot 12 H_2O$ (0.10 mole) and 33.0 grams of magnesium bis (diethyl orthophosphate) $Mg[OP(O)(OEt)_2]_2$ (0.10 moles) was mixed with 20 ml. of water, evolving heat of reaction to warm the mixture from 20° C. to 35° C. To this reaction product was added 10 ml. more water and 250 ml. benzene, and the mixture was heated to reflux while stirring vigorously for one hour. The water phase was allowed to settle, and the green benzene phase was decanted and filtered, yielding upon evaporation 28.2 grams of green, brittle glassy material.

Analysis of the unpurified material indicated 10.8% by weight trivalent chromium (theoretical 10.2 wt. percent). This product decomposed without melting upon heating above 250° C., but readily dissolved in polar organic solvents including methylene chloride or chloroform. Molecular weight measured by melting point lowering of camphor was found to be 2850 and 2350 at 10% and 5% by weight in camphor respectively. This indicated polymeric structures of the formula $Cr[OP(O)(OEt)_2]_3$ from 4 to 6 units per molecule.

EXAMPLE II

Preparation of Chromium (III) Tris (di-2-chloroethyl orthophosphate)

A mixture composed of 11.8 grams magnesium bis (di-2-chloroethyl phosphate) (0.025 mole), 4.44 grams of chromic chloride hexahydrate $CrCl_3 \cdot 6 H_2O$ (0.0167 mole) and 15 ml. $H_2O$ was heated to 50° C. The cooled product solution was extracted with 50 ml. chloroform, and evaporation of the chloroform yielded about 1.0 grams bright green resinous material containing the desired composition.

EXAMPLE III

Use of Chromic Tris (di-2-chloroethyl orthophosphate) for Ethylation of Benzene

A 2 liter stirred autoclave was purged with ethylene gas and was charged with 500 ml. dry benzene and 1.0 grams ethyl aluminum sesquichloride. A solution containing 0.2 gram chromic tris (di-2-chloroethyl orthophosphate) catalyst prepared in Example II was charged into one addition funnel, and 1.0 gram ethyl aluminum sesquichloride co-catalyst was charged into a separate funnel.

The reactor was pressured to 20 psig. with ethylene gas and maintained at this pressure throughout the reaction, while the catalyst and co-catalyst were metered into the reactor over a 20-minute period. Reaction temperature of 25° C. was maintained constant by external cooling throughout the 90-minute reaction period. Analysis of the liquid reaction product indicated 25 grams monoethyl benzene was formed during the reaction.

EXAMPLE IV

Use of Chromic Tris (diethyl Orthophosphate) for Propylation of Naphthalene

Into a 2 liter stirred autoclave dried and purged with propylene was charged 130 grams naphthalene (1.0 mole) and 500 ml. of n-heptane. A catalyst mixture containing 0.344 gram chromic tris (diethylorthophosphate) prepared as in Example I and 1.0 gram ethyl aluminum sesquichloride in 15 ml. methylene chloride and 15 ml. benzene was injected into the reactor. Propylene pressure was maintained around 20 psig. while 2.0 grams ethyl aluminum sesquichloride was added throughout the reaction to maintain the reaction temperature around 40° C. A total of 180 grams (4.3 moles) propylene was completely reacted within 90 minutes. Molar percentages of the alkylated naphthalenes as indicated by gas chromatography analysis of the solvent free product were as follows:

| | |
|---|---|
| Unreacted Naphthalene | 6.9% |
| Monoisopropyl Naphthalene | 20.9% |
| Diisopropyl Naphthalene | 10.8% |
| Triisopropyl Naphthalene | 20.3% |
| Tetraisopropyl Naphthalene | 13.9% |
| Penta and Hexaisopropyl Naphthalene | 27.0% |

About 12 grams of the propylene was converted to trimethyl cyclohexane. The tetraisopropyl naphthalene was found to consist largely of the 1,3,5,7 isomer.

EXAMPLE V

Use of Chromic Tris (diethyl orthophosphate) Polymerization of Isobutylene

The reactor described in Example IV was cleaned, dried and purged with propylene monomer gas. The catalyst mixture as prepared in Example IV was charged with 1.0 gram additional ethyl aluminum sesquichloride into the reactor, followed by 30 grams propylene monomer to initiate the reaction.

A source of isobutylene gas at 40 psig. was connected to the autoclave and the exothermic reaction was maintained at 50° C. for 100 minutes. The light yellow oil reaction product weighed 2138 grams. This product was only slightly soluble in methanol. Viscosity at 38° C. was measured to be 900 centipoise, typical of low molecular weight polyisobutylene ranging in degree of polymerization from 100 to 1000 monomeric units.

The isobutylene polymer product was analyzed and found to consist of a bimodal distribution of molecular weights with a number average of 510. The ratio of weight average to number average of this distribution was found to be 1.9. In most respects the product was similar to that normally produced with aluminum chloride catalysts, except for the distribution of unsaturation associated with each molecule:

| Distribution of Unsaturation Bond Types | |
|---|---|
| Tetrasubstituted [$R_2C=CR_2$] | 45% |
| Trisubstituted [$R_2C=CRH$] | 36% |
| Vinylidene [$R_2C-CH_2$] | 19% |

The vinylidene content was found very high in comparison with polymers produced from isobutylene by aluminum chloride, indicating a unique chain termination mechanism operated in the novel catalyst system. This residual unsaturation is particularly useful for further reaction of the polymer with other reagents containing unsaturated groups or groups which normally react with unsaturated compounds. Maleic anhydride was found appreciably more reactive with this polymer product than with isobutylene polymers produced by aluminum chloride catalysts.

EXAMPLE VI

Use of Chromic Tris (diethyl orthophosphate) Polymerization of Ethylene

A clean, stirred 2 liter reactor was purged with ethylene gas, and 1300 ml. of dry heptane was charged. A solution containing 0.6 gram of chromic tris (diethylorthophosphate) catalyst in 40 ml. benzene was charged into one addition funnel. Into a separate addition funnel was charged 1.2 grams of diethyl aluminum chloride co-catalyst in 40 ml. of heptane.

Ethylene monomer gas regulated at 30 psig. was connected to the reactor throughout the course of reaction. Catalyst and co-catalyst were metered at the same rate into the reactor over a 15-minute period. During the two hours following the start of catalyst addition, the reaction exotherm raised the autoclave from 20° C. to 45° C. The reaction product was filtered to recover solid polyethylene, which was washed with isopropanol and dried and weighed 45 grams. The polyethylene product was typical of high molecular weight, medium density polyethylene (0.919 grams/cc.) and softened above 120° C. to a drawable melt.

I claim:
1. The method comprising
   1. mixing at least two components from (A) a chromium tris-diorgano-orthophosphate of the formula $Cr[OP(O)(OR)_2]_3$ in which each R is selected from the class consisting of non-aromatic hydrocarbon groups free of aliphatic unsaturation and containing one to eight carbon atoms, non-aromatic hydrocarbon ether groups free of aliphatic unsaturation and containing three to six carbon atoms and chlorinated and brominated derivatives thereof, (B) an alkyl aluminum halide of the general formula $R'_c Al X_d$ in which each R' is an alkyl group of one to six carbon atoms, each X is a halogen atom, each $c$ and $d$ is 1 or 2 and the total of $c$ and $d$ is 3, the mol ratio of (A) to (B) ranging from 1:1 to 1:20, and (C) at least one aliphatic, cycloaliphatic and/or aromatic olefin containing no more than about 20 carbon atoms;
   2. adding the remaining component, if any, the mol ratio of total (A) and (B) to (C) ranging from 0.0001:1 to 0.01:1;
   3. heating the mixture at a temperature and for a time sufficient to initiate the reaction of component (C); and separating the resulting product from the reaction mixture.

2. The method of claim 1 wherein prior to the addition of component (C) there is added component (D) at least one aromatic hydrocarbon containing from 6 to about 14 aromatic carbon atoms, the mol ratio of total (A) and (B) to the total (C) and (D) ranging from 0.0001:1 to 0.01:1.

3. The method of claim 1 wherein said three components are mixed in a common inert solvent which is liquid at all temperatures employed.

4. The method of claim 3 wherein said solvent is a low molecular weight chloroalkane.

5. The method of claim 2 wherein component (C) is ethylene and the mol ratio of (D) to (C) is less than 0.01:1.

6. The method of claim 1 wherein component (C) consists essentially of isobutylene.

7. The method of claim 2 wherein component (C) is propylene and the mol ratio of (D) to (C) is at least 0.01:1.

8. The method of claim 2 wherein said aromatic hydrocarbon is unsubstituted.

9. The method of claim 2 wherein said aromatic hydrocarbon is substituted with substituents selected from the group consisting of chlorine atoms, bromine atoms, alkyl groups, alkenyl groups, ether groups, cyclic ether groups, and nitrite groups.

* * * * *